United States Patent [19]

Gralnick

[11] Patent Number: 5,332,670
[45] Date of Patent: Jul. 26, 1994

[54] MONOCLONAL ANTIBODY AGAINST HUMAN PLATELETS

[75] Inventor: Harvey R. Gralnick, Kensington, Md.

[73] Assignee: The United States of America as represented by the Department of Health and Human Services, Washington, D.C.

[21] Appl. No.: 815,882

[22] Filed: Jan. 7, 1992

Related U.S. Application Data

[63] Continuation of Ser. No. 432,380, Nov. 3, 1989, abandoned.

[51] Int. Cl.$^5$ .................. C12N 5/12; C07K 15/28
[52] U.S. Cl. .................. 435/240.27; 530/388.25
[58] Field of Search ............... 530/388.25; 435/240.27

[56] References Cited

U.S. PATENT DOCUMENTS 4,783,330  11/1988  Furie et al. ............... 436/519
4,820,505  4/1989   Ginsberg et al. ........... 436/501

OTHER PUBLICATIONS

McEver, R. P., et al., Journal of Biological Chemistry, vol. 259, No. 15, Aug. 10, 1984, pp. 9799–9804.
Boukerche, H., et al., Medline, Abstract No. 88111698, Eur. J. Biochem., 171(1-2):383–92, Jan. 15, 1988.
Kelton, J. G., et al., Biological Abstracts, vol. 83(11), Abstract No. 108012, 1987.
Tuszynski, G. P., et al., Biological Abstracts, vol. 86(7), Abstract No. 66138, 1988.
Kambayashi, H., et al., "Leucocyte Typing III—White Cell Differentiation Antigens", edited by McMichael, A. J., et al, issued 1987 by Oxford University Press, p. 787.
Hsu-Lin et al, J. Bio. Chem. 259, 14, pp. 9121–9126 Jul. 1984.
Stenberg et al, J. Cell Bio. 101 pp. 880–886 Sep. 1985.
McEver, Blood Cells (1990) 16:73–83.

*Primary Examiner*—David L. Lacey
*Assistant Examiner*—Susan A. Loring
*Attorney, Agent, or Firm*—Birch, Stewart, Kolasch & Birch

[57] ABSTRACT

A novel anti-platelet monoclonal antibody which is without effect on inactivated platelets, but which augments platelet aggregation after minimal perturbation of the platelets, and various applications of the monoclonal antibody are described.

2 Claims, 5 Drawing Sheets

FIG. 1
1 2 3
200—
116.2—
92.5—
66— 

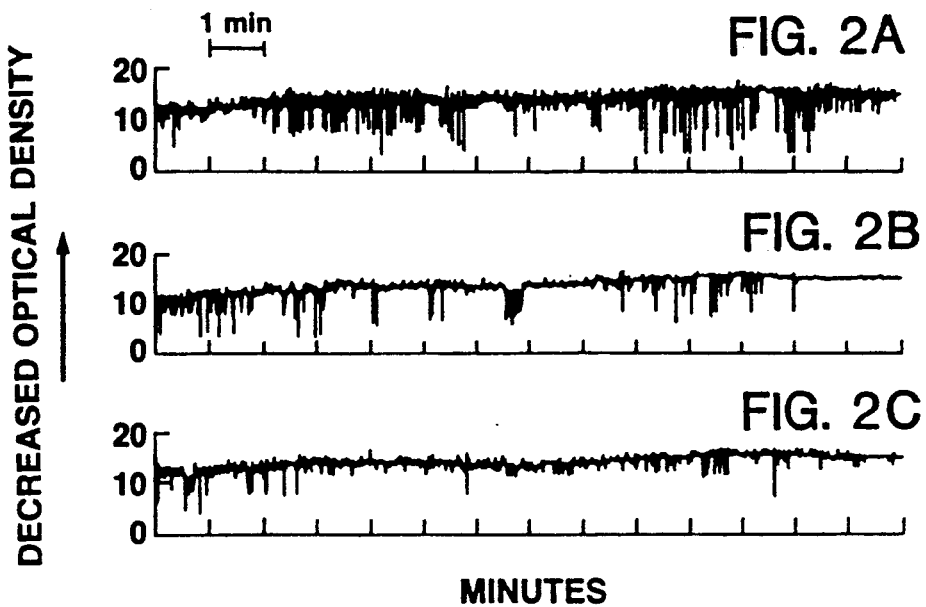
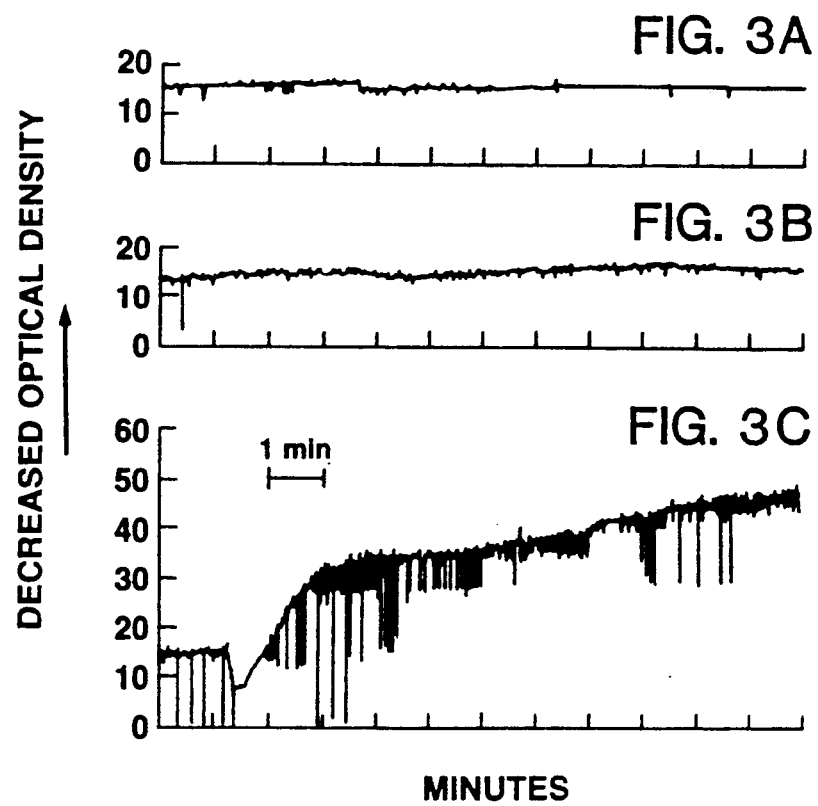

MINUTES

MONOCLONAL ANTIBODY AGAINST HUMAN PLATELETS

This application is a continuation, of application Ser. No. 07/432,380 filed on Nov. 3, 1989, now abandoned.

The present invention is related generally to monoclonal antibodies. More particularly, the present invention is related to a unique monoclonal antibody (MAb) against human platelets, said MAb being designated herein as 8G8 and which binds to about $6.5 \times 10^3$ sites per platelet only after activation of resting platelets, with a kD of about 5 nM. Such a monoclonal antibody has not heretofore been known or described.

BRIEF DESCRIPTION OF THE DRAWINGS

Various features and attendant advantages of the invention will be better understood upon a reading of the following detailed description when considered in connection with the accompanying drawings wherein:

FIG. 1 demonstrates that this antibody recognizes a protein on the surface of thrombin stimulated platelets which is of different molecular weight from those previously described. In lane 3 is the monoclonal antibody 8G8. In lane 2 is a monoclonal antibody which recognizes the GMP 140 and the monoclonal antibody in lane 1 recognizes the glycoprotein Ia/IIa complex, molecular weight of approximately 157 and 136. The estimated molecular weight of the protein recognized by 8G8is 148 kD. FIGS. 2A-2C show that when platelet-rich plasma is placed in the aggregometer and no agonist is added, there is no platelet aggregation (FIG. 2A). When the antibody 8G8 was added at 20 mM/ml or 40 mM/ml, FIGS. 2B and 2C respectively, they did not induce platelet aggregation. Thus indicating that these antibodies by themselves cannot initiate platelet aggregation.

FIGS. 3A-3C show that when adenosine diphosphate (ADP) is added to platelets (FIG. 3A) at a concentration of 3 $\mu$M, platelet aggregation does not occur. When the antibody 8G8is added to platelets at a concentration of 10 ug/ml (FIG. 3B), it does not initiate platelet aggregation. As shown in FIG. 3C, the addition of ADP at a dose of 3 $\mu$M and the addition at 10 $\mu$g/ml of antibody 8G8causes platelet aggregation and the release reaction.

In FIG. 4A at 35 $\mu$g/ml of collagen no platelet aggregation occurs. There is a dose response relationship between the amount of platelet aggregation and the amount of antibody 8G8added to these sub-threshold amount of collagen and platelets. FIG. 4B, 40 $\mu$g/ml of monoclonal antibody plus collagen. FIG. 4C, 20 $\mu$g/ml of monoclonal antibody plus collagen. FIG. 4D, 10 $\mu$g/ml of monoclonal antibody plus collagen, and FIG. 4E, 2 $\mu$g/ml of monoclonal antibody plus collagen.

In FIGS. 5A-5C.

DETAILED DESCRIPTION OF THE INVENTION

Various objects and advantages of the present invention are achieved by producing a monoclonal antibody 8G8which, inter alia, has the following properties.

(a) Belongs to subclass IgG1.

(b) Unlike other monoclonal antibodies which bind to resting human platelets, this MAb binds only after activation of the resting human platelets. Antibody 8G8recognizes a 148,000 molecular weight protein on the surface of normal and stimulated platelets (FIG. 1). This antibody recognizes 425 sites/platelet on resting platelets with a kD of 2nM; in contrast, platelets that have been activated by thrombin express $6,500 \pm 1,500$ sites with a kD of 5.7 nM. With ADP as the agonist, the number of sites per platelet are about 7,000 with a kD of 4.7 nM. This antibody requires the presence of cations for binding to the antigen. Calcium is more effective than magnesium. EDTA completely blocks the binding of this antibody to resting or activated platelets.

(c) Distinctive from other platelet related MAbs, this MAb is without effect on nonactivated human platelets in the presence or absence of calcium or in the presence or absence of plasma proteins; however, in the presence of calcium and plasma protein, this MAb is capable of augmenting the effect of non-aggregating doses of platelet agonists to cause platelet aggregation, but only if there has been at least a slight or minimal perturbation (activation) of platelets (FIGS. 2-5). In other words, unperturbed or inactivated platelets remain unaffected by this MAb.

Figure 4A:
FIGS. 4A-4E shows similar results when collagen is used as the agonist.
Figure 4B:
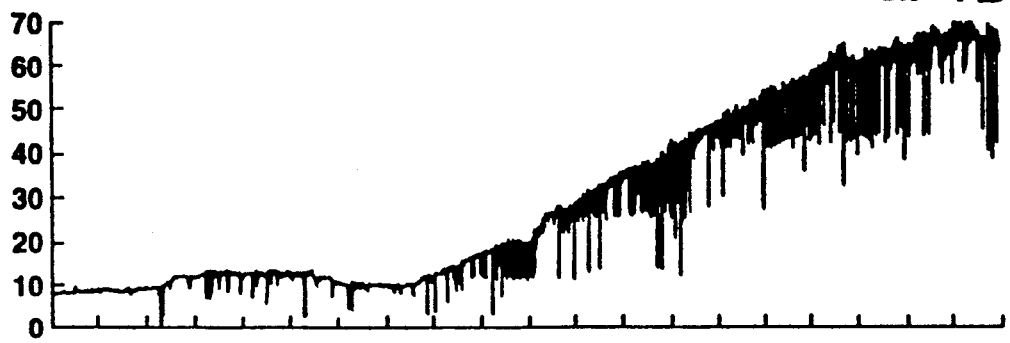
Figure 4C:
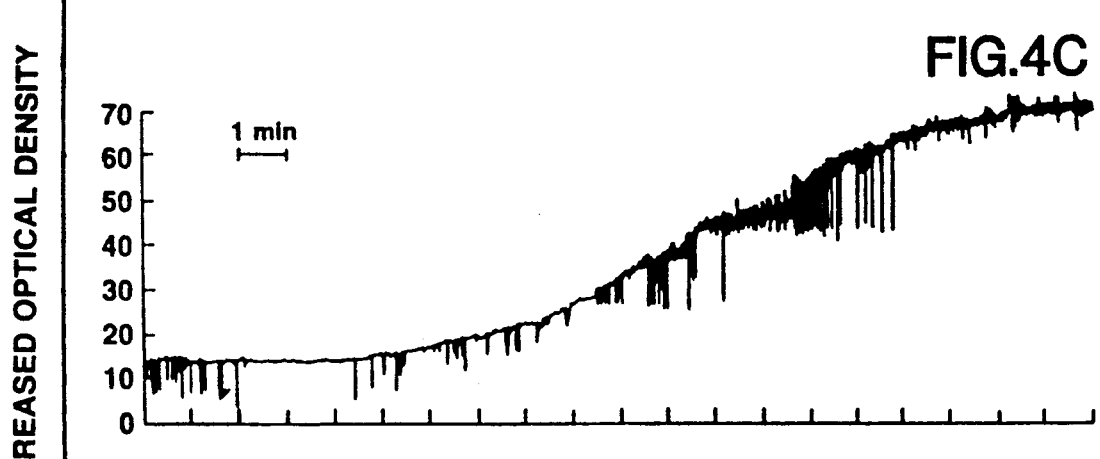
Figure 4D:
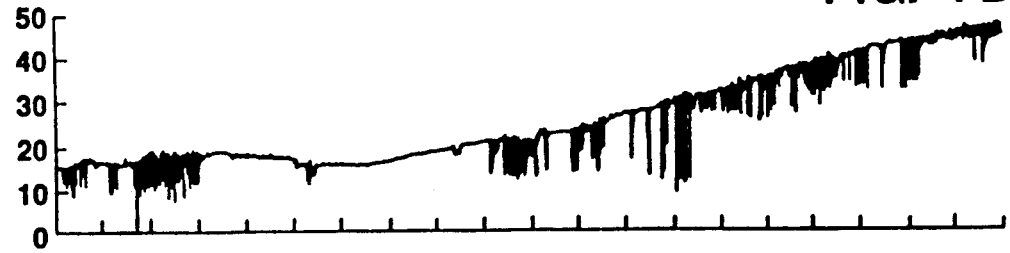
Figure 4E:
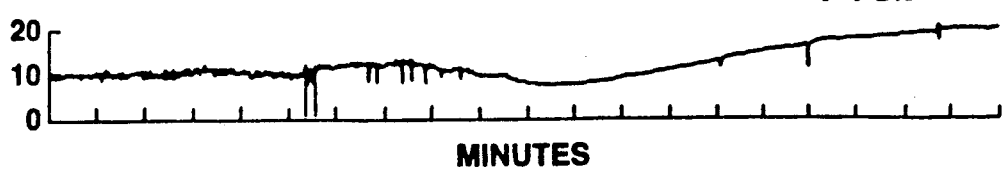
Figure 5A:
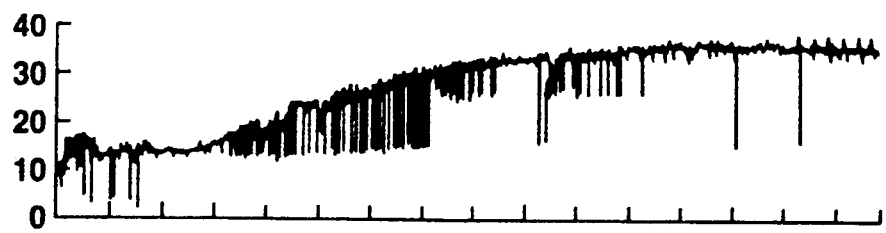
FIG. 5A is the addition of 7.5 $\mu$M of epinephrine to platelet-rich plasma and a small primary wave of platelet aggregation occurs, but there is no secondary wave nor release.
Figure 5B:
In FIG. 5B the addition of 10 $\mu$g/ml of antibody 8G8by itself to platelets has no effect on the platelet aggregation. However, in FIG. 5C the addition of the 10 $\mu$g/ml of 8G8 to platelet-rich plasma that has been partially stimulated by 7.5 $\mu$g/ml epinephrine results in a primary and a secondary wave of platelet aggregation and the release reaction.
Figure 5C:
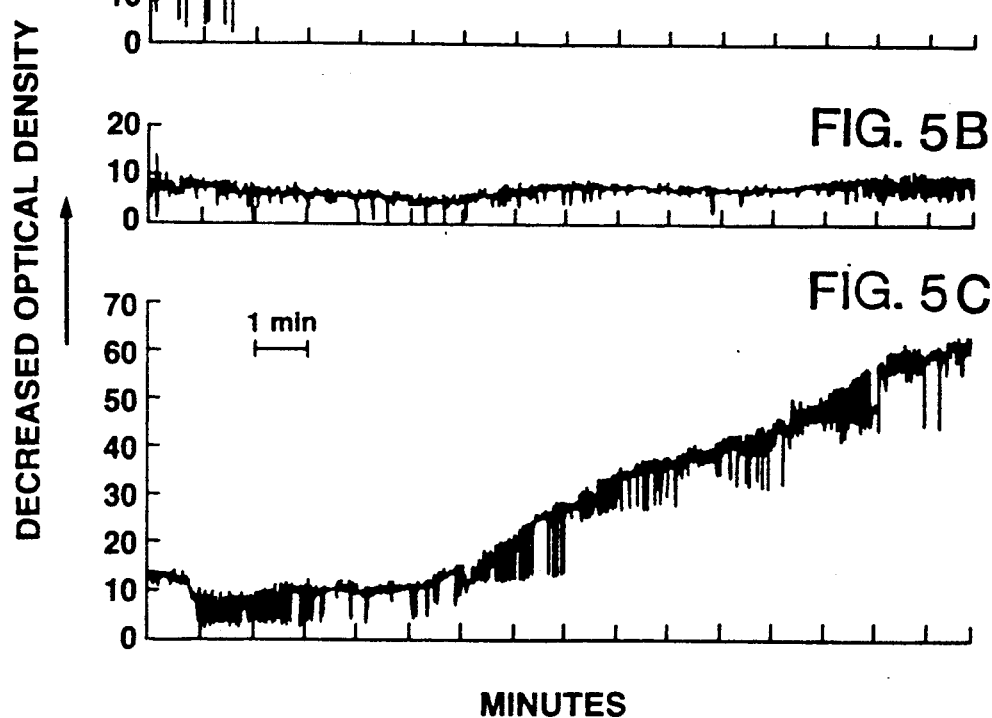
Figure 6A:
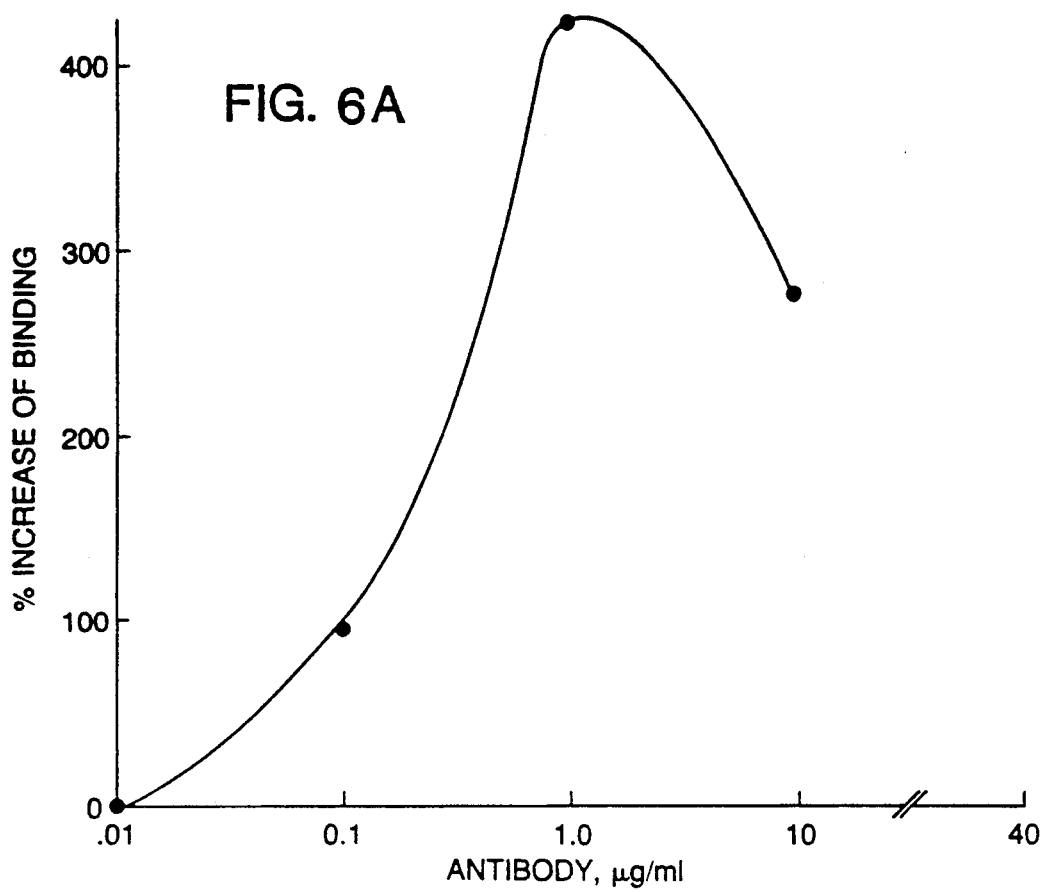
FIGS. 6A and 6B show the dose effect of the antibody 8G8on ligand binding when added to platelets stimulated with 3 $\mu$M ADP. In these tests, the platelets were incubated with the ADP. The antibody 8G8 was added followed by the radiolabelled fibrinogen or von Willebrand factor. As the dose of the antibody 8G8is increased from 0.1 to 10 $\mu$g/ml, there is over a 400% increase in the amount of von Willebrand binding (6A) and a 1200% increase in the amount of fibrinogen binding (6B). Similar results were obtained using epinephrine or collagen as the agonist.
Figure 6B:
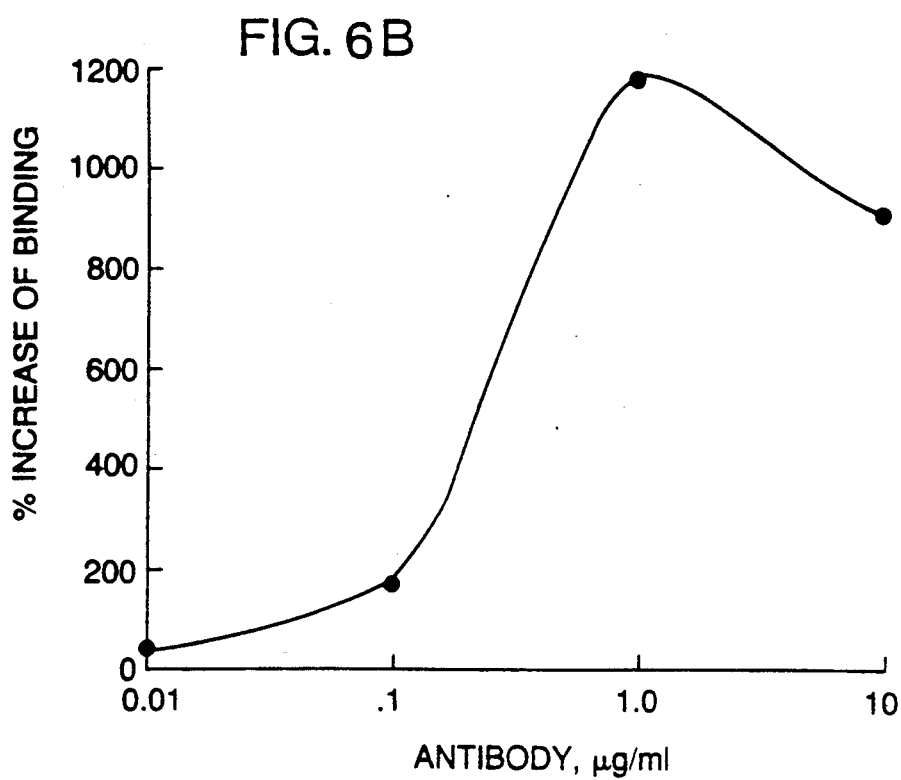

(d) Enhances the binding of fibrinogen, von Willebrand factor and fibronectin to platelet surface, but is without effect on thrombospondin binding to human platelets (FIG. 6A and 6B).

Thus, 8G8is an antibody which binds to human platelets after minimal activation with high affinity and markedly increases the amount of activation dependent events involved in platelet aggregation even in the presence of dosages of agonist which by themselves are ineffective in causing platelet aggregation.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred materials and methods are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "substantially unreactive" as used herein means that the reaction, If any, of the antibody with the resting human platelets is so minimal that it is of no significance or consequence and is virtually undetectable by routine techniques.

MATERIALS AND METHODS

The immunogen used for production of the monoclonal antibody 8G8 was stimulated platelets that had been formalin fixed after 5 minutes incubation with thrombin. Before stimulation and fixation, the platelets were purified from other cells and plasma proteins by centrifugation on arabinogalactan gradient (5 ml of 10% and 3 ml of 20%). The platelets were prepared from whole blood by centrifugation at 600 g for 3 minutes at room temperature (22°-24° C.). Platelet-rich plasma was removed and was separated from plasma proteins and lymphocytes on an arabinogalactan gradient. These platelets, free of other cellular contamination, were then activated with thrombin 0.1 u/ml, final concentration, per $1 \times 10^8$ platelets. After 5 minutes, the platelets were mixed with equal volume of 2% formalin. Three injections of these cells were made into BALB/c mice prior to the fusion. The fusion was performed with PU mouse myeloma cells and murine splenocytes with poly ethylene glycol. At 7-10 days, the wells were inspected for growth positivity. Supernatants were screened for antibody production by a standard ELISA technique and by flow cytometry. The positive individual cells selected by the screening procedures were then expended to 24 macrowell plates containing H-T media, and murine spleens feeder cells. When supernatant from the macrowells were tested and found to be positive, these clones were then subjected to limiting dilution studies, the 8G8 underwent 6 limiting dilutions. The fused cells were then injected intraperitoneally in pristine BALB/c, and ascites fluid was collected after 2-3 weeks. The antibody was purified by chromatography over a protein-A Sepharose column. The antibody, 8G8, was found to belong to the Ig1 subclass.

Fusion Procedure

1. Seven days before fusion, pass PU mouse myeloma cells at $3.5 \times 10^5$/ml in complete media with 1% 8-azaguanine (10-20 g/ml) total volume 100 ml. On the fifth day after addition of 8-azaguanine, add 100 ml complete media to culture. On the sixth day, centrifuge cells 100 rpm $10^1$, and resuspend in complete media at a concentration of $3.5 \times 10^5$ cells/ml. On the seventh day cells should be in mid log phase $4-6 \times 10^5$/ml. For each fusion, take $3 \times 10^7$ PU cells and wash in RPMI 1640 with glutamine, Penicillin-streptomycin (pen-strep). (Note no FCS at this step). Resuspend in 1 ml RPMI with glutamine, pen-strep.

2. Autoclave PEG for 15'. Dilute v/v with RPMI (Glutamine, pen-strep) and add 1 drop sterile 7.5% sodium bicarbonate for each ml of 50% PEG.

3. Remove immunized mouse spleen aseptically and place in small petri dish containing 8 ml RPMI+-glutamine+2× pen-strep. Use small sterile syringe plunger to homogenize spleen. Transfer spleen to 15 ml centrifuge tube and rinse petri with 2 ml RMPI+-glutamine+2× pen-strep. Let spleen settle 1-2' to get rid of large debris. Remove 9.5 ml and add to washed $3 \times 10^7$ PU cells. Spin at 1400 rpm for 10'. Aspirate off as much supernatant as possible. Gently tap test tube over top of test tube rack to spread out cell pellet. Add 1 ml 50% PEG at 37° C. dropwise over one minute to cell pellet. Add 5 ml RPMI (glutamine, pen-strep) over 5 minutes (add 1 ml in drops over 1 minute, then add 4 ml and wait 4 minutes). Fill tube with RPMI (glutamine, pen-strep) a second time and centrifuge 1000 rpm 10'. Resuspend pellet in 100 ml selective cloning media and place in 5 microtiter 96-well flat bottom plates. Cover/-wrap with parafilm and plate in 37° C., 7% $CO_2$ incubation.

4. At 7-10 days inspect wells for growth positivity and acidification of media (yellowing of media). When positive, supernatants must be screened for antibody production and/or antibody specificity by standard ELISA protocol.

5. Individual wells selected by screening procedure are then expanded to 24 macrowell plates containing H-T media and murine spleen feeder cells. Ideally, a limiting dilution (LD) is to be carried out immediately at the time of supernatant positivity; however, it can be carried out at the macrowell step. Regardless of procedure followed, the parenteral "clone" should be cryopreserved as soon as possible.

6. For LD, obtain cell count and viability on clone. Also prepare spleen feeder cells (1 spleen for five plates suspended in 10 ml of HT as per step 3). Essentially want 100 hybridoma cells per 96-well plate and approximately $2 \times 10^5$ spleen feeder cells/well. LD should be carried out ×3 to ensure clonal origin of hybridoma. Subclones from each LD and final clones should be cryopreserved.

Complete Media
  RPMI 1640: Biofluids Cat. #102
  50 ml Fetal calf serum 309 (heat inactivated): Gibco Cat. #240-6309
  10 ml L-glutamine: Gibco Cat. #320-5030
  0.5 ml Gentamicin: Gibco Cat. #600-5710
RPMI 1640: Biofluids VCat. #102
  10 ml L-glutamine: Gibco Cat. #320-5030
  5.0 ml Penicillin-Streptomycin mixture: M.A. Bioproducts Cat. #17-6034
CDME
  450 ml DMEM: Biofluids Cat. #104
  0.474 ml Penicllin-streptomycin mixture: M.A. Bioproducts Cat. #17-6034
  9.47 ml 200 mM L-glutamine: Gibco Cat. #320-5030
  59.3 ml FCS (heat inactivated): Gibco Cat. #240-6309
  4.74 ml Nonessential amino acids: M.A. Bioproducts Cat. #173-114A
  2.84 ml Sodium pyruvate: Gibco Cat. #320-1360
  59.3 ml NCTC 109: Gibco Cat. #320-1340
Selective cloning media
  99 ml CDME
  1.0 ml HAT (hypoxanthine, aminopterin, thymidine): Hazelton Cat. #59-77076
PEG 1500 (polyethylene glycol ): M.A. Bioproducts, Cat. #17-7802
HT
  (Hypoxanthine, Thymidine): Hazelton Cat. #59-57076
  99 ml CDME
  1.0 ml HT
Costar 96-2311 flat-bottom tissue culture plates: Cat. #3596

A deposit of the hybridoma secreting NAb 8G8 has been made at the American Type Culture Collection, 12301 Parklawn Dr., Rockville, Md. 20852-1776, on Oct. 24, 1989 under accession number HB10273. The deposit shall be viably maintained, replacing if it becomes non-viable during the life of the patent, for a period of 30 years from the date of the deposit, or for 5 years from the last date of request for a sample of the deposit, whichever is longer, and upon issuance of the patent made available to the public without restriction In accordance with the provisions of the law. The Commissioner of Patents and Trademarks, upon request, shall have access to the deposit.

Specificity of 8G8

Data presented in FIGS. 1-6A and 6B provide evidence of various properties of 8G8 listed herein above.

Utility of 8G8

The antibody 8G8 can be employed for the purpose of in vitro detecting activated platelets. This antibody which only binds to activated platelets also enhances the expression of other activation-dependent proteins such as von Willebrand factor or fibrinogen. Thus, this antibody could be used in vitro as a probe for detection of activated platelets in a variety of disease states. These disease states include thrombosis, embolization, activation of coagulation, and certain bleeding disorders.

The assay could be performed by employing the antibody 8G8in either a flow cytometer or by fluorescence microscopy to detect if it bound to platelets in vitro. It would also be useful because this antibody would enhance the expression of other activation-dependent proteins which would make it easier to detect activated platelets by other assays.

This antibody may also be important in vitro in individuals who have thrombocytopenia, qualitative platelet defects or other defects in blood coagulation. This antibody could be given intravenously and it would only identify and bind to slightly activated platelets and could enhance their activation process making them more hemostatically competent. This would result in an agent which could be used to reduce surgical bleeding in normal as well as hemostatically compromised individuals. It could also be used topically in the form of a liquid or impregnated In gauze or a band aid to superficial skin wounds to enhance blood coagulation, wound healing, and to arrest bleeding. This antibody could be used either in its native form or it could be pharmacologically bound to a carrier which would enhance its intravascular survival and increase the potency of the antibody in augmenting platelet activation, the release reaction and platelet aggregation. These steps are all important in normal hemostasis. A kit could be provided containing the antibody 8G8or the antibody 8G8could be administered by its impregnation in a variety of dressings to help arrest wound bleeding.

This antibody may also be used in the diagnosis of activated platelets, as a method of monitoring antithrombotic therapy directed against activated platelets, and platelet activation to be used as a hemostatic agent in the arrest of bleeding in major surgical procedures as well as minor wounds, abrasions, etc. This antibody can be used to explore a whole new field of understanding platelet activation. This is the first known antibody which identifies a 148,000 kD protein present only on activated platelets which is different from GMP140. 8G8 binds to a 148 kD and in doing so augments the binding of ligands to platelets and platelet aggregation. The mechanism by which this antibody functions biochemically remains to be determined.

The availability of the anti-platelet MAb 8G8also allows the preparation of antihemorrhagic composition containing an effective amount of 8G8to react with activated platelets, and a pharmaceutically acceptable carrier well known to one of ordinary skill in the art, such as physiological saline, non-toxic sterile buffer and the like. A kit comprises a container containing the antibody 8G8, either cryopreserved or otherwise.

As would be suggested to one of ordinary skill in the art, by employing standard techniques this antibody could be conjugated with antithrombotic agents, fibrinolytic drugs, anti-platelet medication or the like to deliver the same to sites of platelet activation, thrombi or emboli for treatment purposes.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A cell line consisting of cells which secrete an antibody having all of the identifying characteristics of the antibody secreted by the hybridoma deposited as HB 10273.

2. An antibody having all of the identifying characteristics of the antibody secreted by the hybridoma deposited as HB 10273.

* * * * *